United States Patent
Hu

(10) Patent No.: US 8,404,287 B2
(45) Date of Patent: Mar. 26, 2013

(54) **USE OF *FRUCTUS SCHISANDRAE* AND EXTRACTS THEREOF IN PREVENTING AND DECREASING TOXIC AND SIDE EFFECTS OF ANTINEOPLASTIC DRUGS**

(75) Inventor: Xun Hu, Hangzhou (CN)

(73) Assignee: Zhe Jiang Dinghui Pharm Co. Ltd., Hangzhou, Zhejiang (CN)

( * ) Notice: Subject to any disclaimer, the term of this patent is extended or adjusted under 35 U.S.C. 154(b) by 0 days.

(21) Appl. No.: 12/027,783

(22) Filed: Feb. 7, 2008

(65) Prior Publication Data

US 2009/0022831 A1    Jan. 22, 2009

Related U.S. Application Data

(63) Continuation-in-part of application No. PCT/CN2006/001975, filed on Aug. 4, 2006.

(30) Foreign Application Priority Data

Aug. 8, 2005  (CN) .......................... 2005 1 0060335
Aug. 8, 2005  (CN) .......................... 2005 1 0060336

(51) Int. Cl.
*A61K 36/00*    (2006.01)
(52) U.S. Cl. ....................................... 424/777
(58) Field of Classification Search ........................ None
See application file for complete search history.

(56) References Cited

U.S. PATENT DOCUMENTS

2005/0123628 A1*  6/2005  Zabrecky ...................... 424/725

FOREIGN PATENT DOCUMENTS

CN    1600330    *    3/2005

OTHER PUBLICATIONS

Bast (Cardiovascular Toxicol. (2007), vol. 7, pp. 154-159).*
Wattanapitayakul (Basic and Clinical Pharmacology and Toxicology (Jan. 2005), vol. 96, pp. 80-87 and the title page).*
English translation of CN 16003330—Mar. 2005.*
The Merriam-Webster's Collegiate Dictionary (10th edition, 1997) p. 924.*
Hancke et al. "Schisandra cinensis (Turcz.) Baill", Fitoterapia, vol. 70, Issue 5 (Oct. 1999) 451-471.*
Qiangrong et al. "Schisandrin B—A novel inhibitor of P-glycoprotein". Biochem Biophys Res Comm, vol. 335, Issue 2 (Sep. 23, 2005) 406-411. Available online Jul. 28, 2005.*
Shan et al. "Anthracycline-Induced Cardiotoxicity". Ann Intern Med 125 (1996) 47-58.*
Yim et al. "Schisandrin B protects against myocardial ischemia-reperfusion injury by enhancing myocardial glutathione antioxidant status". Mol Cell Biochem. 196 (1999) 151-156.*
Zhang et al. "Action of schizandrin B, an antioxidant, on lipid peroxidation in primary cultured hepatocytes". Zhongguo Yao Li Xue Bao. Jul. 1989;10(4):353-6. (Abstract only).*

* cited by examiner

*Primary Examiner* — Amy L Clark
(74) *Attorney, Agent, or Firm* — Osha Liang LLP

(57) ABSTRACT

Use of *Fructus schisandrae* in preparation of medicaments for preventing and reducing toxicity and side effects of antineoplastic agents. The toxicity and side effects of antineoplastic agents are cardiovascular toxicity, hepatotoxicity, nephrotoxicity, suppression of bone marrow, immunosuppression, or alopecia etc induced by antineoplastic agents. *Fructus schisandrae* and extracts thereof, especially ethanol extracts, schisandrin B, are effective in reducing antineoplastic agent's toxicity and side effects.

2 Claims, 7 Drawing Sheets

USE OF FRUCTUS SCHISANDRAE AND EXTRACTS THEREOF IN PREVENTING AND DECREASING TOXIC AND SIDE EFFECTS OF ANTINEOPLASTIC DRUGS

FIELD OF THE INVENTION

The invention is directed to the use of *Fructus Schisandrae* and extracts thereof in preventing and reducing toxicity and side effects of antineoplastic agents.

BACKGROUND ARTS

Tumor is one of the main causes that leads to human death. Chemotherapy is a main approach to treat tumor. However, antineoplastic agent may result in various toxic and side effects, including cardiovascular toxicity, hepatotoxicity, nephrotoxicity, suppression of bone marrow, immunosuppression, and alopecia, etc.

*Fructus Schisandrae* is the mature dry fruit of *Schisandra chinensis* (Turcz.) Baill. or *Schisandra sphenanthera* Rehd. Et Wits. *Fructus Schisandrae* was regarded as a top grade Chinese traditional medicine in an ancient book named "Shennong Ben Cao Jing". Dibenzocyclooctadiene lignans (Dibenzocyclooctane lignan) are the main ingredient of *Fructus Schisandrae*, which is the mature dry fruit of *Schisandra chinensis* (Turcz.) Baill. or *Schisandra sphenanthera* Rehd. Et Wils. It was described in the book that *Fructus Schisandrae* had the function of astringency, arresting discharge, nourishing qi to generate fluid, and tonifying kidney to relieve mental stress. It is an usual medicine for strengthening by tonification in traditional Chinese medicine. It has various pharmacological actions, but it was not reported that *Fructus Schisandrae* and dibenzocyclooctadiene lignans could also prevent and reduce the toxic and side effects produced by an antineoplastic agent.

SUMMARY OF THE INVENTION

An object of the invention is to provide a new use of *Fructus Schisandrae* and its extracts, i.e., the use in preventing and reducing toxicity and side effects of antineoplastic agent.

To achieve the objective, the invention provides the following technical solutions:

Use of *Fructus schisandrae* in the preparation of a medicament for preventing and reducing the toxicity and side effects of antineoplastic agent.

The toxicity and side effects of antineoplastic agent include cardiovascular toxicity, or hepatotoxicity, or nephrotoxicity, or suppression of bone marrow, or immunosuppression, or alopecia, etc., caused by antineoplastic agent.

Use of the extracts of *Fructus schisandrae* in the preparation of a medicament for preventing and reducing the toxicity and side effects of antineoplastic agent.

The toxicity and side effects of antineoplastic agent include cardiovascular toxicity, or hepatotoxicity, or nephrotoxicity, or suppression of bone marrow, or immunosuppression, or alopecia, caused by antineoplastic agent.

The extracts of *Fructus schisandrae* are those extracted by organic solvents from *Fructus schisandrae* or those obtained by the supercritical fluid extraction. The extracts extracted by ethanol are preferred.

The extract of *Fructus schisandrae* is dibenzocyclooctadiene lignan. Dibenzocyclooctadiene lignan has a core structure represented by formula 1 (J Chang, J Reiner, J. Xie. Chem. Rev. 2005, 105, 4581-4609).

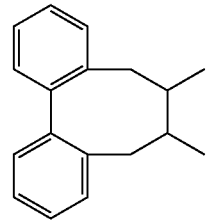 [SMILES: CC1Cc2ccccc2-c2ccccc2CC1C]

Concretely, the structure of the dibenzocyclooctadiene lignan is represented by formula (I):

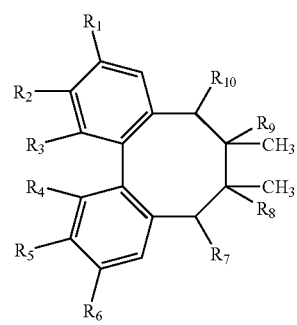

Wherein, $R_1$, $R_2$, $R_5$, $R_6$ is independently hydroxyl or methoxyl, or, R1 and R2, and R5 and R6 independently take together to form an alkoxyl ring, or they independently do not form a ring;

$R_3$ is selected from the group consisting of:

①

②

③

④

$R_4$ is selected from the group consisting of:

①

②

③

$R_7$ is selected from the group consisting of:

① 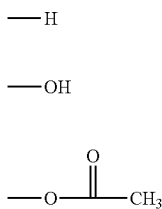

②

③

④ 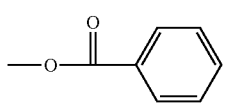

⑤ 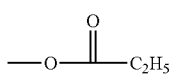

⑥ 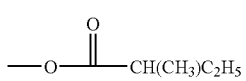

⑦ 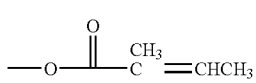

⑧ 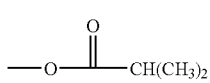

$R_8$, $R_9$ is independently selected from the group consisting of:
① —H
② —OH $R_{10}$ is selected from the group consisting of:

① -H

② -OH

③ 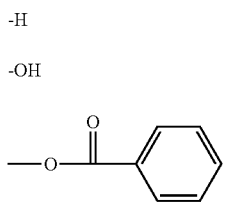

④ 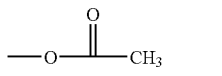

⑤ 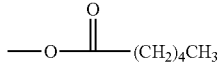

⑥ 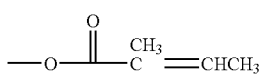

or, $R_7$ and $R_{10}$ take together to form an oxygen bridge, wherein $R_1$-$R_6$, $R_9$, and $R_9$ are defined as above;

or, $R_3$ and $R_7$ take together to form an acyloxy ring, wherein $R_1$, $R_2$, $R_4$-$R_6$, $R_8$-$R_{10}$ are defined as above.

Preferably, the dibenzocyclooctadiene lignan is selected from the group consisting of:

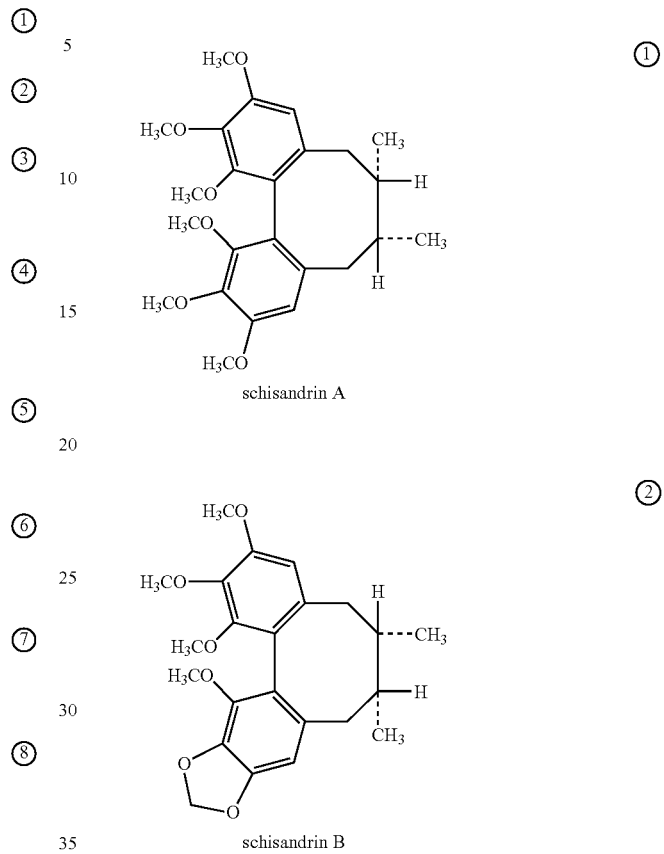

schisandrin A schisandrin B

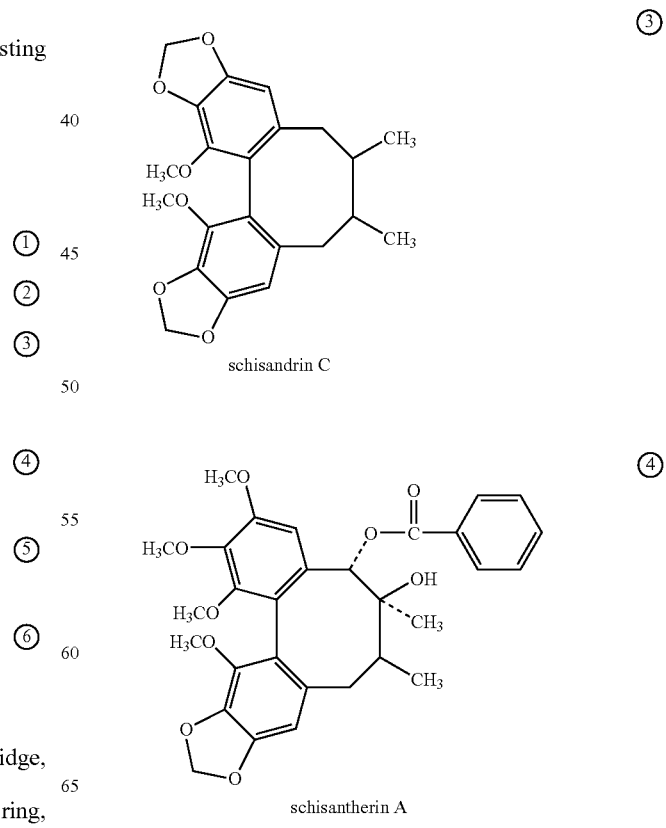

schisandrin C schisantherin A

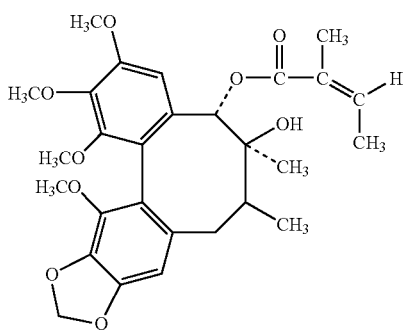
schisantherin B

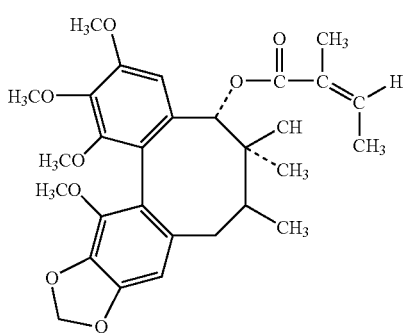
schisantherin C

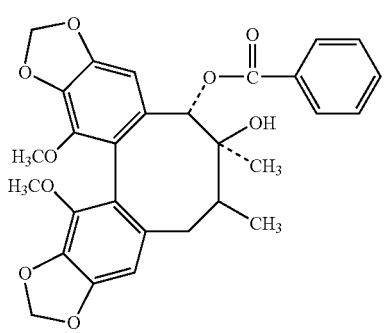
schisantherin D

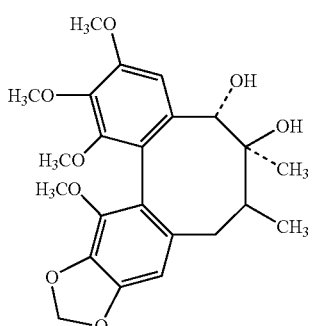
schizandrol A

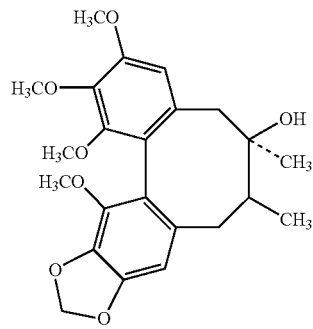
schizandrol B

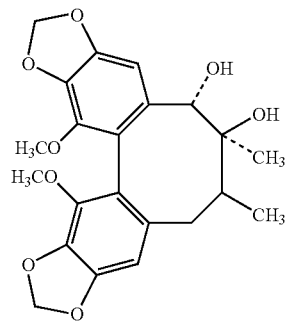
schizandrol C

Preferably, the dibenzocyclooctadiene lignan is schisandrin B.

The antineoplastic agent, the toxicity and side effects of which can be prevented or reduced by *Fructus Schisandrae* and its extracts as described above, is selected from the group consisting of aclarubicin, amrubicin, carubicin, daunorubicin, detorubicin, doxorubicin, epirubicin, esorubicin, galarubicin, idarubicin, ladirubicin, leurubicin, medorubicin, nemorubicin, pirarubicin, rodorubicin, sabarubicin, valrubicin, zorubicin, Bleomycin A5, Bleomycin, Pirarubicin, Dactinomycin, Aclarubicin, Mitomycin, Etoposide, Teniposide, Homoharringtonine, Hydroxycamptothecin, Topotecan, Paclitaxel, Docetaxel, Vincristine, Catharanthus Alkaloid, Vindesine, Vinorelbine, Lentinan, Tamoxifen, Formestane, Exemestane, Anastrozole, Letrozole, Toremifene, Flutamide, Bicalutamide, 5-fluorouracil, Cytarabine, Tegafur, Furtulon, fluridine, Mercaptopurine, Methotrexate, Gemcitabine, Capecitabine, Cytoxan, Ifosfamide, Busulfan, Melphalan, Chlorambucil, Semustine, Alestramustine, Mesna, Cisplatin, Carboplatin, Oxaliplatin, Dacarbazine, Asparaginase, Clodronate Disodium, Pamidronate disodium, Etidronate disodium, Ibandronate, Herceptin, Iressa, Mitoxantrone, Hydroxycarbamide, Methylcantharidnimide, Norcantharidin, Cinobufacini, Ubenimex, Arsenic Trioxide, AiDi, Amifostine, Matrine, Imatinfb, Sodium glycididazole, Dianhydrogalactitol, Procarbazine.

Preferably, the antineoplastic agent is an anthracycline antibiotic.

The medicine, which can prevent and reduce toxicity and side effects of antineoplastic agent, can be one dibenzocyclooctadiene lignan alone, or can be a mixture of two or more dibenzocyclooctadiene lignans.

*Fructus schisandrae* and dibenzocyclooctadiene lignan, the extract of *Fructus schisandrae*, can be used in the preparation of a medicament for improving cardiac function.

Drug excipients and carriers can be added with the medicine that can prevent and reduce toxicity and side effects of antineoplastic agent to prepare one of the following dosage forms: injection solution, tablet, capsule, granule, and decoction.

The *Fructus Schisandrae* and its extracts of the present invention can produce good clinical foreground in preventing and reducing toxicity and side effects of antineoplastic agent. *Fructus Schisandrae* and its extracts, especially the ethanol extracts and schisandrin B, can effectively reduce the toxicity and side effects caused by antineoplastic agent, especially the side effects such as cardiovascular toxicity, or hepatotoxicity, or nephrotoxicity, or suppression of bone marrow, or immunosuppression, or alopecia etc., caused by antineoplastic agent. The invention also illustrates that *Fructus Schisandrae* and its extracts have good effect on improving cardiac function.

DETAILED DESCRIPTION OF THE INVENTION

Figure 1:
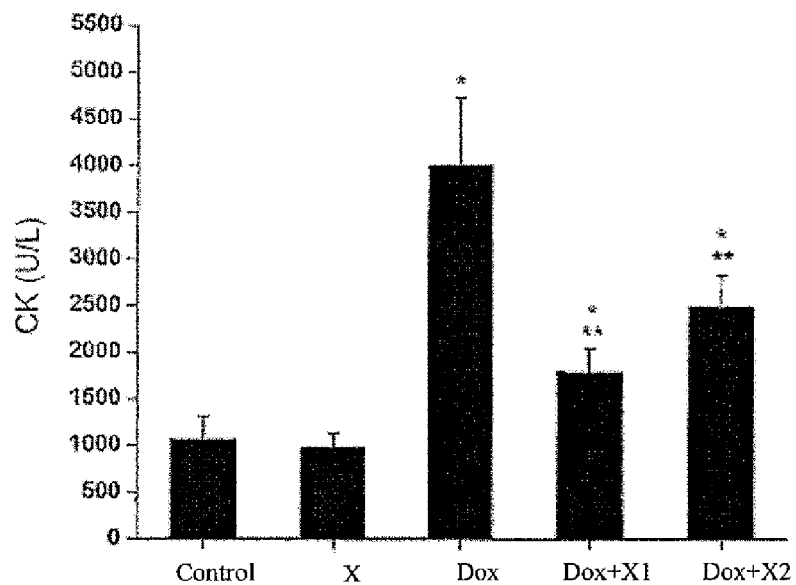
FIG. 1 shows that the ethanol extracts of *Fructus schisandrae* can inhibit the increase of mouse serum myocardium enzyme, creatine kinase (CK), induced by Doxorubicin.
Figure 2:
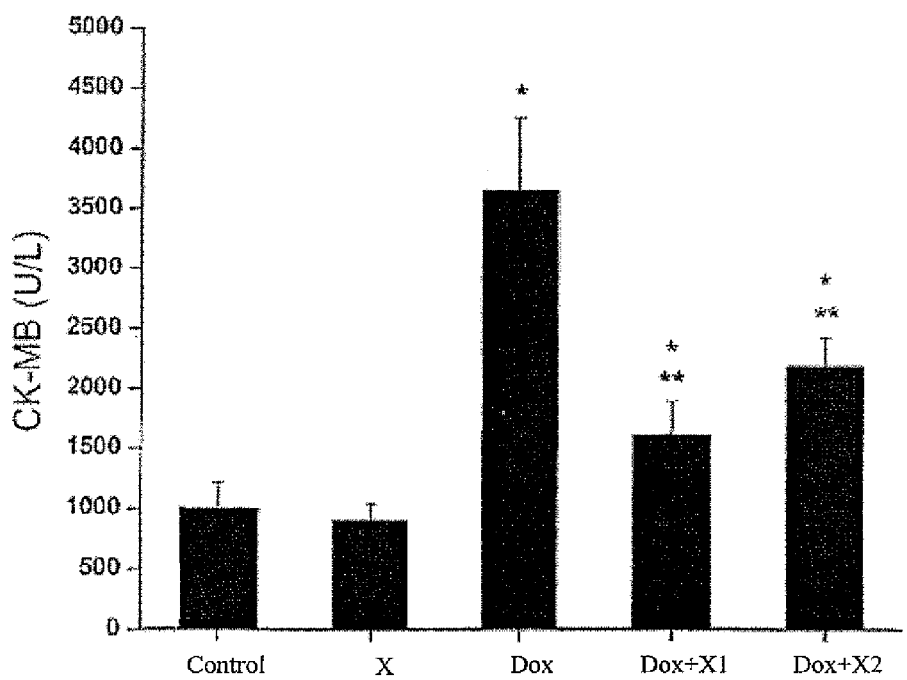
FIG. 2 shows that the ethanol extracts of *Fructus schisandrae* can inhibit the increase of mouse serum myocardium enzyme, creatine kinase isozyme (CK-MB), induced by Doxorubicin.
Figure 3:
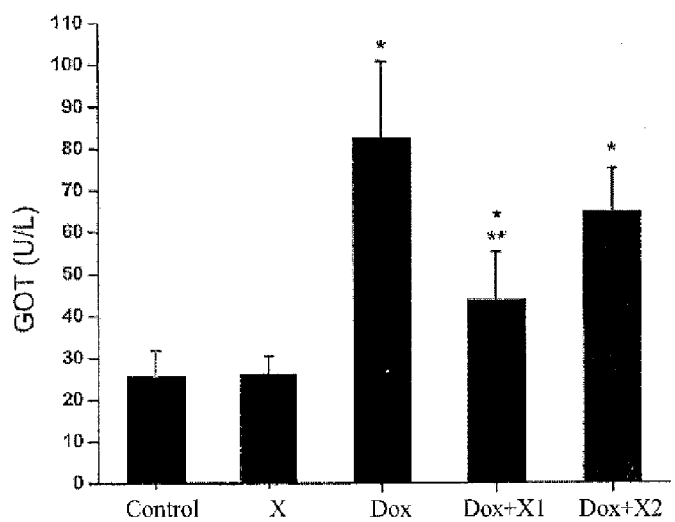
FIG. 3 shows that the ethanol extracts of *Fructus schisandrae* can inhibit the increase of mouse serum myocardium enzyme, glutamic-oxalocetic transaminase (GOT), induced by Doxorubicin.
Figure 4:
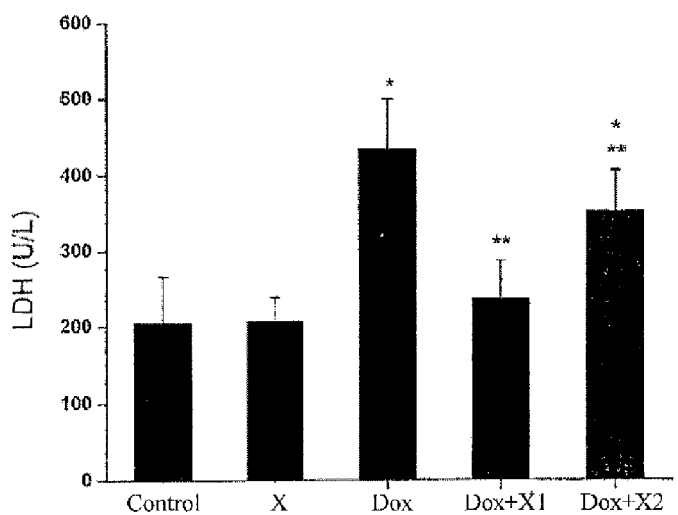
FIG. 4 shows that the ethanol extracts of *Fructus schisandrae* can inhibit the increase of mouse serum myocardium enzyme, lactic dehydrogenase (LDH), induced by Doxorubicin.

The invention is further illustrated by the following examples. These examples are only intended to illustrate the invention, but not to limit the scope of the invention.

Example 1

Preparation of the Ethanol Extract of *Fructus Schisandrae*

Percolation Method: 5000 g of *Fructus schisandrae* powder was percolated with 85-95% ethanol in an amount of 6 times of the mass of the powder. The percolation velocity is 15 ml/min. The ethanol leachate was recycled. The ethanol was recycled under reduced pressure until there was no ethanol odor. The leachate was concentrated to obtain an extractum with density of 1.15 g/ml, which was ready for use. The ethanol can be replaced by other alcohols, such as methanol, propanol, etc. Other organic solvents, such as ethyl acetate, ether, etc. can also be used to replace ethanol to prepare the extract of *Fructus schisandrae*.

Example 2

The Ethanol Extract of *Fructus schisandrae* can Prevent Toxicity and Side Effects Induced by Doxorubicin 1. Materials and Methods
1.1 Drugs and Agents
Doxorubicin Hydrochloride Injection was obtained from Italy pharmacia Co. (Product No.: 5E2002-D). Ethanol extract of *Fructus schisandrae* prepared from Example 1 was dissolved in 0.5% Poloxamer. CK (creatine kinase), CK-MB (creatine kinase isozyme), LDH (lactic dehydrogenase) and GOT (glutamic-oxalocetic transaminase) were detected by automatic biochemistry analyzer. Tissue Protein extraction solution was obtained from American Pierce Co. Male ICR mice with a body weight of 25-30 g were obtained from Shanghai Experimental Animal Center.
1.2 Grouping and Administration
150 animals were divided randomly into 5 groups.

Control group: 24 mice were dosed intragastrically with normal saline in an amount of 20 ml/kg each time at the $1^{st}$-$3^{rd}$ day of the experiment, once a day. At the $3^{rd}$ day, the mice were injected with normal saline in an amount of 25 ml/kg into their abdominal cavities within 2 hours after drench.

Group of the ethanol extract of *Fructus schisandrae* (the X group): 24 mice were dosed intragastrically with the ethanol extract of *Fructus schisandrae* in an amount of 400 mg/kg each time at the $1^{st}$-$3^{rd}$ day of the experiment, once a day.

Group of Doxorubicin (the Dox group): 42 mice were dosed intragastrically with normal saline in an amount of 20 ml/kg each time at the $1^{st}$-$3^{rd}$ day of the experiment, once a day. At the $3^{rd}$ day, the mice were injected with Doxorubicin of 25 mg/kg into their abdominal cavities.

Group 1 of Doxorubicin plus the extract of *Fructus schisandrae* (group 1 of Dox +X): 24 mice were dosed intragastrically with the extract of *Fructus schisandrae* in an amount of 400 mg/kg each time at the $1^{st}$-$3^{rd}$ day of the experiment, once a day. At the $3^{rd}$ day, the mice were injected with 25 mg/kg of Doxorubicin into their abdominal cavities 0.5 hours after drench.

Group 2 of Doxorubicin plus the extract of *Fructus schisandrae* (group 2 of Dox +X): 24 mice were dosed intragastrically with the extract of *Fructus schisandrae* in an amount of 200 mg/kg each time at the $1^{st}$-$3^{rd}$ day of the experiment, once a day. At the $3^{rd}$ day, the mice were injected with 25 mg/kg of Doxorubicin into their abdominal cavities 0.5 hours after drench.

1.3 Detection of Serum Myocardium Enzymes

At the $5^{th}$ day (48 hours after injection of Doxorubicin into abdominal cavity), blood were collected. The serum was separated by regular separation and frozen at −80° C. CK, CK-MB, LDH and GOT were determined by automatic biochemistry analyzer.

1.4 Detection of Myocardium Matrix Metalloproteinase (MMP-2)

Sample Preparation

The mice were put to death by cervical dislocation after obtaining their blood and were dissected quickly to obtain the hearts. The left ventricular was separated, washed clean with normal saline and weighed. The left ventricular myocardium tissues were taken out, triturating under liquid nitrogen. 500 μl pre-cooling extraction buffer (10 mmol/L Tris-HCL, pH7.5, 1 mmol/L $MgCl_2$, 1 mmol/L EGTA, 0.1 mmol/L PMSF, 5 mmol/L β-mercaptoethanol, 5 g/L CHAPS, 0.01% Triton X-100) was added. The mixture was put on the ice for 10 min, then centrifuged at 15000 g for 30 min. The supernatant was removed for detecting protein concentration by Bradford detection. 20 μl sample was added with 5× sample buffer (not including mercaptoethanol) 5 μl and were hold for 15 min under 37° C.

10% SDS-PAGE gel was prepared as separating gel (including 0.1% glutin), which is covered with 4% concentrating gel. 20 μl sample after treatment was loaded onto the gel to carry out electrophoresis with 40 mA constant current under a temperature of below 4° C. After electrophoresis, the gel was hold in the eluent (2.5% Triton X-100, 50 mmol/L Tri HCL, 5 mmol/L $CaCl_2$, 1 μmol/L $ZnCl_2$, pH7.6), agitated and eluted for 2 times, 45 min/time. The gel was then put in the rinsing solution (the eluent without Triton X-100) for rinsing for 2 times, 20 min/time. The gel was then put in the incubation solution (50 mmol/L Tri HCl, 5 mmol/L $CaCl_2$, 1 μmol/L $ZnCl_2$, 0.02% Brij 35, pH7.6) for incubation for 18 h under 37° C. The gel was stained with the staining solution (0.05% Coomassie brilliant blue, 30% methanol, 10% acetic acid) for 3 h. After the gel was decolorated for 0.5 h, 1 h, and 2 h by using decoloration solution A, B, and C (containing methanol in a concentration of 30%, 20%, 10% respectively and acetic acid in a concentration of 10%, 10%, 5% respectively), respectively, matrix metalloproteinase (MMP) was showed as a transparent brilliant strip against the blue background. The gel was scanned by UVP gel scanner and was kept in the archives. The electrophoretogram was analyzed by GelWorks ID Advanced v4.01 software to determine the density of bands digested by gelatinase.

1.5 Survival Rate Observation

The remainder mice were observed for 7 days from the day of administering Doxorubicin and the change of survival rate was recorded.

2. Results 2.1 Effect of the Extract of *Fructus schisandrae* on Serum Myocardium Enzyme Spectrum of Mice with Myocardial Damage Induced by Doxorubicin There was no significant differences between the serum myocardium enzyme spectrum indexes, including CK, CK-MB, LDH, GOT, of the control group and those of the X group (P>0.05). The 4 serum myocardium enzyme spectrum indexes of the Dox group were significantly higher than those of the control group and the X group (P<0.05). The serum enzyme indexes of the two dosage groups which were administered in combination with the extract of *Fructus schisandrae* were decreased to a certain extent as compared with those of the Dox group. Specifically, the 4 serum enzymology indexes of the group using 400 mg/kg of the extract of *Fructus schisandrae* for 3 times together with Doxorubicin were significantly lower than those of the group using Doxorubicin alone (P<0.05) (see FIGS. 1-4). These indicated that the cardio toxicity induced by Doxorubicin could be effectively prevented by the ethanol extract of *Fructus schisandrae*.

Figure 5:
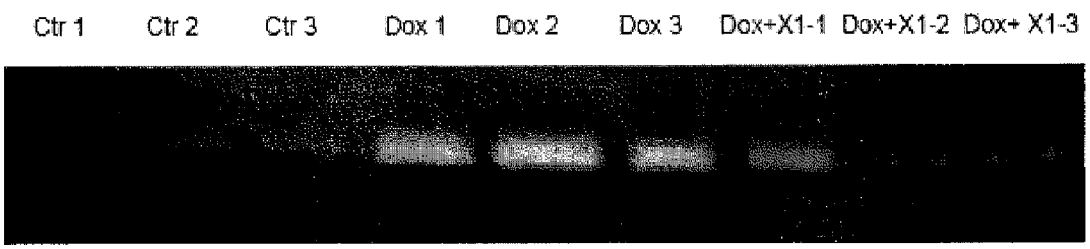
FIG. 5 shows that the ethanol extracts of *Fructus schisandrae* can inhibit the increase of mouse left ventricular myocardium matrix metalloproteinase MMP-2 activity induced by Doxorubicin.

2.2 Detection Results of the Activity of Left Ventricular Myocardium Metalloproteinase No activity of left ventricular myocardium matrix metalloproteinase (MMP-2) were detected both in the normal control group and in the X group. The activity of left ventricular myocardium MMP-2 of the Dox group was increased significantly. The gelatinase activity of left ventricular myocardium MMP-2 were inhibited obviously in both groups using the extract of *Fructus schisandrae* together with Doxorubicin, wherein the inhibition effect of the group using 400 mg/kg of the extract of *Fructus schisandrae* together with Doxorubicin was the best (see FIG. 5). The results indicated that the cardio toxicity induced by Doxorubicin could be effectively prevented by the ethanol extracts of *Fructus schisandrae*.

Figure 6:
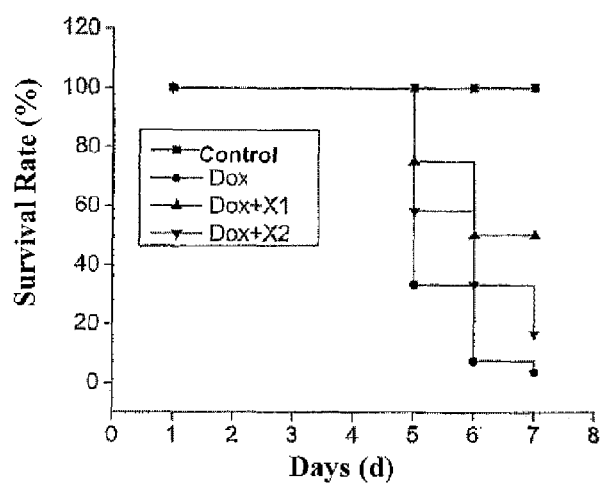
FIG. 6 shows that the ethanol extracts of *Fructus schisandrae* can inhibit the death of mouse induced by Doxorubicin.

2.3 Effect of the Extract of *Fructus schisandrae* on Survival Rate of Mice with Acute Toxicity Induced by Doxorubicin The death of mice in the Dox group and in the two groups of Dox+X occurred on the $5^{th}$ day. On the $7^{th}$ day, the survival rate of the Dox group was 3.7%, the survival rate of the group using 400 mg/kg of the extract of *Fructus schisandrae* for 3 times together with Doxorubicin was 50% (P<0.01), and the survival rate of the group using 200 mg/kg of the extract of *Fructus schisandrae* for 3 times together with Doxorubicin was 16.7% (P<0.05). See FIG. 6. These indicated that toxicity and side effects induced by Doxorubicin could be obviously reduced by the extract of *Fructus schisandrae*.

2.4 Effects of the Ethanol Extract of *Fructus schisandrae* and Doxorubicin on Apparent Condition of Mice Mice in the group using Doxorubicin alone were in bad conditions, manifested as asthenia, listlessness, hypotrichosis. However, mice in the group administered with the extract of *Fructus schisandrae* for 3 times together with Doxorubicin were relatively active and eutrichosis. These indicated that toxicity and side effects induced by Doxorubicin could be reduced by the ethanol extract of *Fructus schisandrae*.

Example 3

The Ethanol Extract of *Fructus schisandrae* Reduces the Cardio Toxicity of Induced by Epirubicin Experimental methods: The ethanol extract of *Fructus schisandrae* obtained in Example 1 was prepared with 0.5% poloxamer as 8 g/ml mutterlauge. ICR mice were purchased from Shanghai Experimental Animal Center. The animals were divided into two groups, 15 mice per group. Each mouse in group 1 was dosed intragastrically with 100 μl solvent (0.5% poloxamer), and each mouse in group 2 was dosed intragastrically with 100 μl ethanol extract of *Fructus schisandrae*, and then mice in each group were injected with 4 mg/kg Epirubicin through tail vein 3 hours after drench of solvent or the ethanol extract. These administrations were carried out once every 7 days for 10 times totally. The mice were put to death one week after the last injection and their hearts were taken out. The heart was fixed with 4% paraform. 48 hours later, the heart was dehydrated with ethanol and fixed with paraffin. The paraffin piece was sliced into sections (with thickness of 2 μm) and the sections were stained with toluidine blue and were observed under microscope. The heart trauma was evaluated by the reported method (Imondi A R, et al. Cancer Research. 1996, 56:4200-4204). The cardio toxicity was evaluated by Severity and Extent. Severity was divided into two grades: Grade 1, which was represented by sarcoplasmic microvacuolation and/or cellular edema and mesenchyme edema; and Grade 2, which was represented by atrophy, necrotic, fibrotic, endocardium trauma and blood clot based on Grade 1. Extent was divided into four grades. Grade 0.5 was represented by less than 10 exceptional myocardium cells within each view of microscope. Grade 1 was represented by more than 10 exceptional myocardium cells within each view of microscope. Grade 2 was represented by dispersal but agminate exceptional myocardium cells. Grade 3 was represented by some agminate exceptional myocardium cells.

The myocardium trauma was calculated by the following formula:

mean total score (MTS)=Σ(S×E)/number of mice in which S is Severity, E is Extent. Higher the mean total score, the severer heart trauma.

Figure 7:
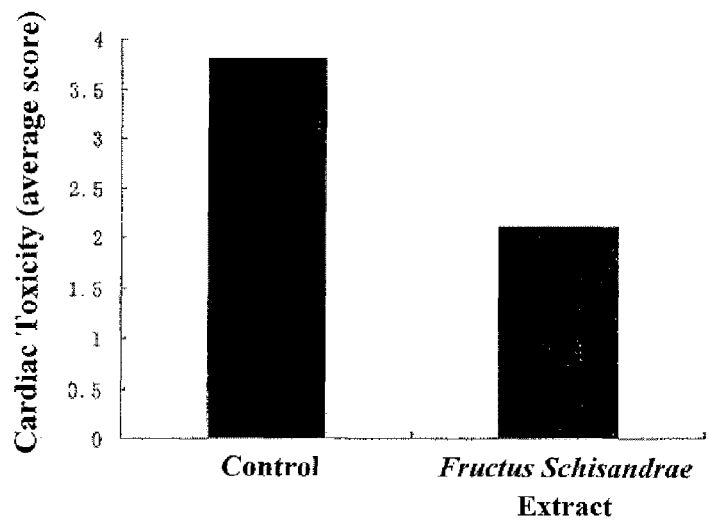
FIG. 7 shows that the ethanol extracts of *Fructus schisandrae* can prevent the cardio toxicity of mouse induced by Epirubicin.

Results: As indicated in FIG. 7, cardio toxicity induced by Epirubicin was significantly prevented by the ethanol extract of *Fructus schisandrae*, i.e., the cardio toxicity induced by Epirubicin could be significantly reduced by the ethanol extract of *Fructus schisandrae*.

Example 4

The Ethanol Extract of *Fructus schisandrae* Reduces Cardio Toxicity Induced by Daunorubicin Experimental methods: The ethanol extract of *Fructus schisandrae* obtained in Example 1 was prepared with 0.5% poloxamer as 8 g/ml mutterlauge. ICR mice were purchased from Shanghai Experimental Animal Center. The animals were divided into two groups, 15 mice per group. Each mouse in group 1 was dosed intragastrically with 100 μl solvent (0.5% poloxamer), and each mouse in group 2 was dosed intragastrically with 100 μl ethanol extract of *Fructus schisandrae*. Then mice were injected with 4 mg/kg Daunorubicin through tail vein 3 hours after drench of solvent or the ethanol extract. These administration were done once every 7 days for 10 times totally. The mice were put to death one week after the last injection and their hearts were taken out. The heart was fixed with 4% paraform. 48 hours later, the heart was dehydrated with ethanol and fixed with paraffin. The paraffin piece was sliced into sections (with thickness of 2 μm) and the sections were stained with toluidine blue and were observed under microscope. The heart trauma was evaluated by the methods as those described in Example 3.

Figure 8:
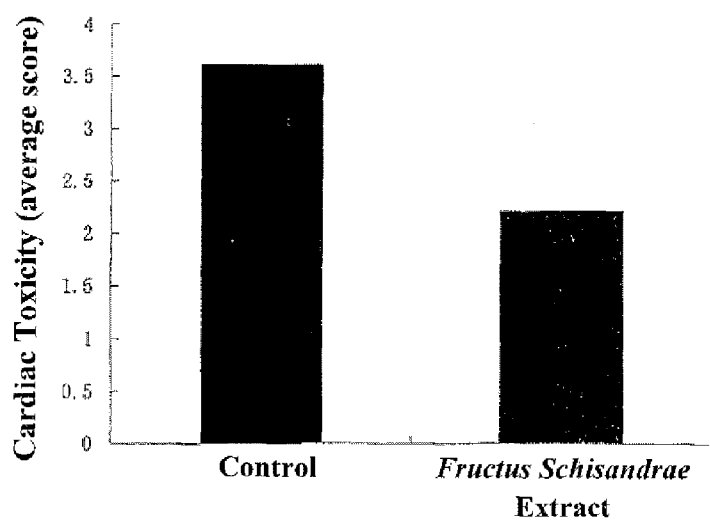
FIG. 8 shows that the ethanol extracts of *Fructus schisandrae* can prevent the cardio toxicity of mouse induced by Daunorubicin.

Results: As indicated in FIG. 8, the cardio toxicity induced by Daunorubicin could be significantly reduced by the ethanol extract of *Fructus schisandrae*.

Example 5

The Ethanol Extract of *Fructus schisandrae* Reduces Cardio Toxicity Induced by Idarubicin Experimental methods: The ethanol extract of *Fructus schisandrae* obtained in Example 1 was prepared with 0.5% poloxamer as 8 g/ml mutterlauge. ICR mice were purchased from Shanghai Experimental Animal Center. The animals were divided into two groups, 15 mice per group. Each mouse in group 1 was dosed intragastrically with 100 μl solvent (0.5% poloxamer), and each mouse in group 2 was dosed intragastrically with 100 μl ethanol extract of *Fructus schisandrae*. Then mice were injected with 4 mg/kg Daunorubicin through tail vein 3 hours after drench of solvent or ethanol extract. These administrations were done once every 7 days for 10 times totally. The mice were put to death one week after the last injection and their hearts were taken out. The heart was fixed with 4% paraform. 48 hours later, the heart was dehydrated with ethanol and fixed with paraffin. The paraffin piece was sliced into sections (with thickness of 2 μm) and the sections were stained with toluidine blue and were observed under microscope. The heart trauma was evaluated by the methods as those described in Example 3.

Figure 9:
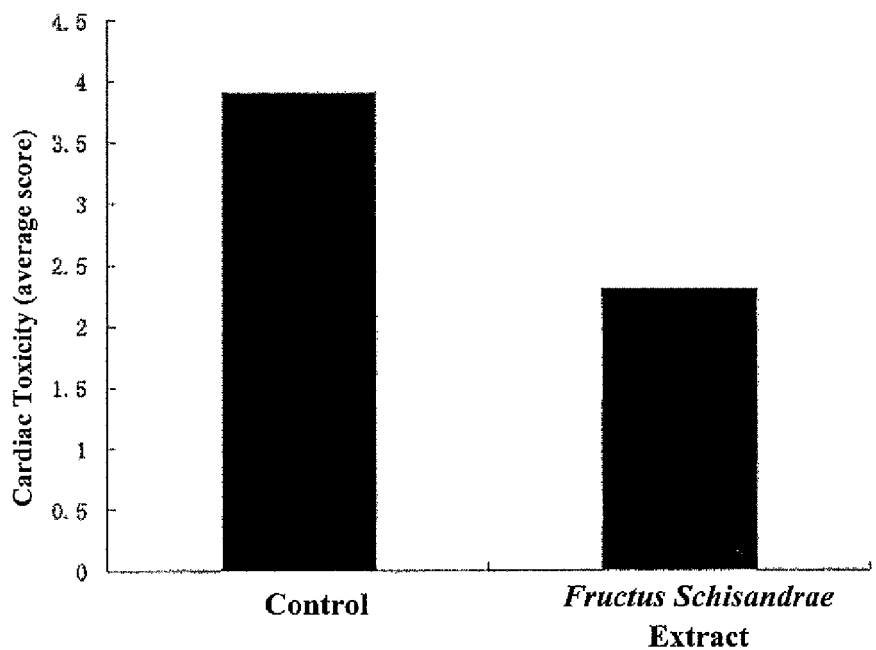
FIG. 9 shows that the ethanol extracts of *Fructus schisandrae* can prevent the cardio toxicity of mouse induced by Idarubicin.
Figure 10:
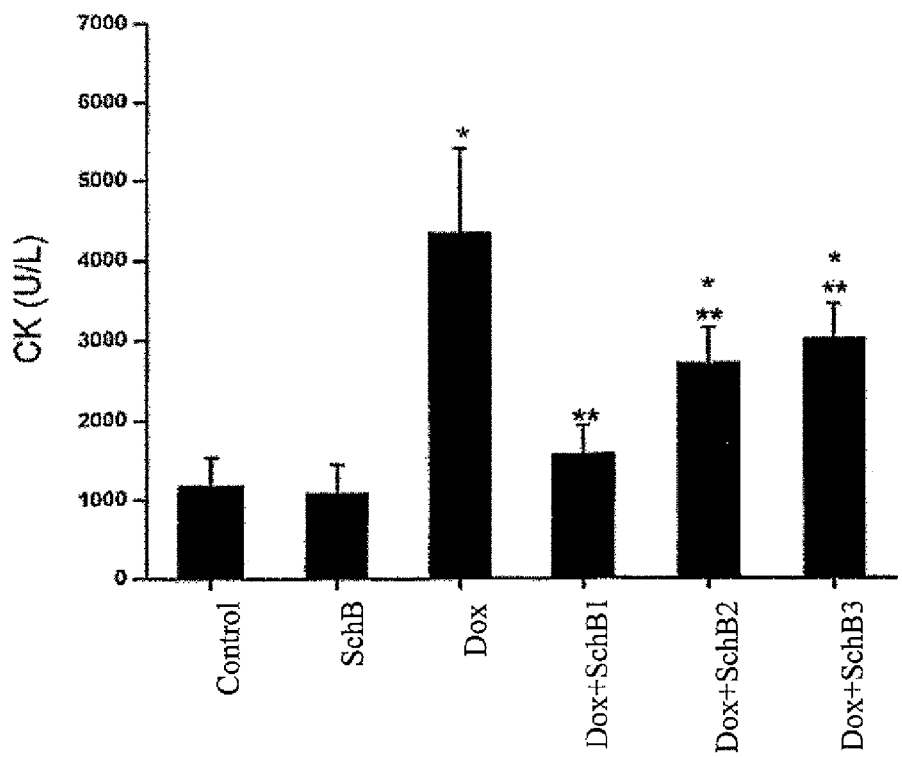
FIG. 10 shows that schisandrin B can inhibit the increase of mouse serum myocardium enzyme, creatine kinase (CK), induced by Doxorubicin.
Figure 11:
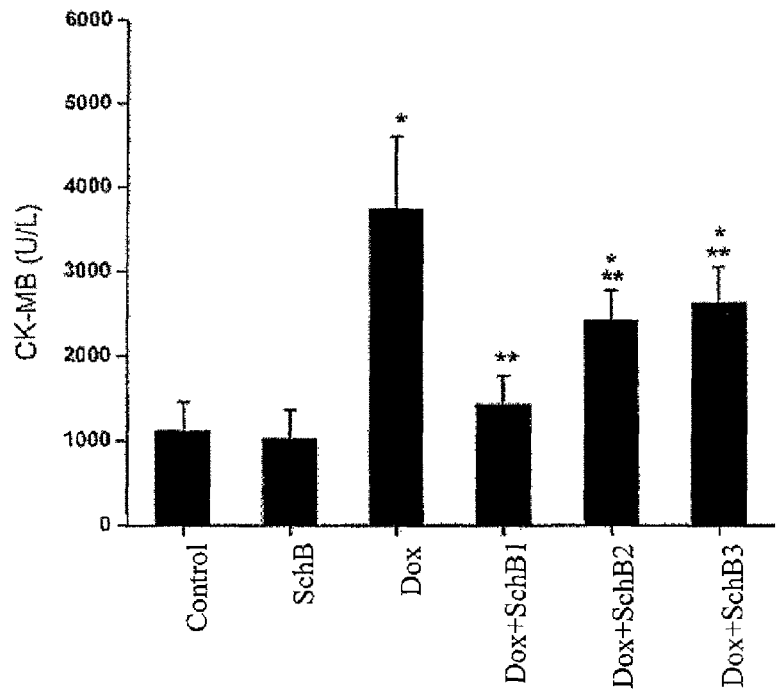
FIG. 11 shows that schisandrin B can inhibit the increase of mouse serum myocardium enzyme, creatine kinase isozyme (CK-MB), induced by Doxorubicin.
Figure 12:
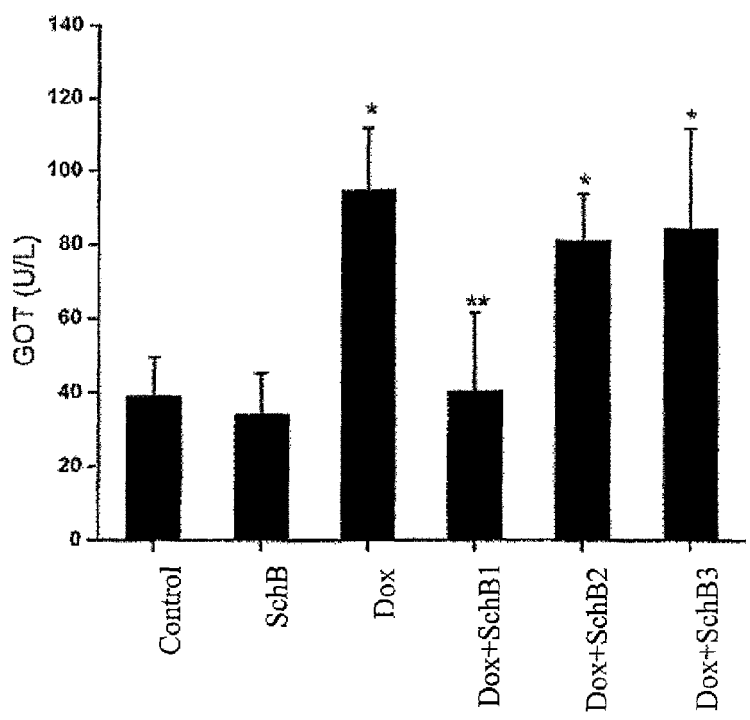
FIG. 12 shows that schisandrin B can inhibit the increase of mouse serum myocardium enzyme, glutamic-oxalocetic transaminase (GOT), induced by Doxorubicin.
Figure 13:
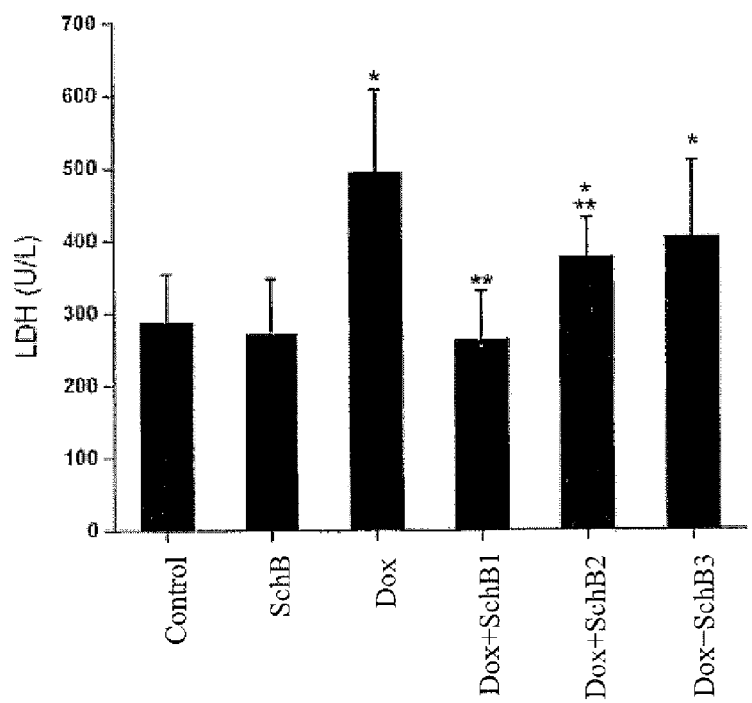
FIG. 13 shows that schisandrin B can inhibit the increase of mouse serum myocardium enzyme, lactic dehydrogenase (LDH), induced by Doxorubicin.

Results: As indicated in FIG. 9, the cardio toxicity induced by Idarubicin could be significantly reduced by the ethanol extract of *Fructus schisandrae*.

Example 6

Prevention of Other Toxicity and Side Effects of Antineoplastic Agent by the Ethanol Extract of *Fructus schisandrae*

1. Materials and Methods
1.1 Experimental Materials

Vincristine, Methotrexate, Cisplatin, Cytoxan, 5-fluorouracil and Doxorubicin were obtained from Shanghai Pharmacy Co. ICR mice with body weight of 20-25 g were from Shanghai Experimental Animal Center. The mice were grouped randomly as below, 6 mice per group.

1.2 Grouping and Administration

Control group: mice were injected into their abdominal cavities with normal saline once every two days, consecutively for 7 times.

Methotrexate group: mice were injected into their abdominal cavities with 2 mg/kg once every two days, consecutively for 7 times.

Group of Methotrexate plus the ethanol extract of *Fructus schisandrae*: mice were dosed intragastrically with 400 mg/kg of the ethanol extract of *Fructus schisandrae*, followed by injection into their abdominal cavities with 2 mg/kg of Methotrexate within 2 hours, once every two days and consecutively for 7 times.

Cisplatin group: mice were injected their abdominal cavities with 2 mg/kg Cisplatin once every two days and consecutively for 7 times.

Group of Cisplatin plus the ethanol extract of *Fructus schisandrae*: mice were dosed intragastrically with 400 mg/kg of the ethanol extract of *Fructus schisandrae*, followed by injection into their abdominal cavities with 2 mg/kg of Cisplatin within 2 hours, once every two days and consecutively for 7 times.

5-fluorouracil group: mice were injected into their abdominal cavities with 30 mg/kg once every two days and consecutively for 7 times.

Group of 5-fluorouracil plus the ethanol extract of *Fructus schisandrae*: mice were dosed intragastrically with 400 mg/kg of the ethanol extract of *Fructus schisandrae*, followed by injection into their abdominal cavities with 30 mg/kg of 5-fluorouracil within 2 hours, once every two days and consecutively for 7 times.

Cytoxan group: mice were injected into their abdominal cavities with 30 mg/kg Cytoxan once every two days and consecutively for 7 times.

Group of Cytoxan plus the ethanol extract of *Fructus schisandrae*: mice were dosed intragastrically with 400 mg/kg of the ethanol extract of *Fructus schisandrae*, followed by injection into their abdominal cavities with 30 mg/kg of Cytoxan within 2 hours, once every two days and consecutively for 7 times.

Vincristine group: mice were injected into their abdominal cavities with 0.3 mg/kg once every two days and consecutively for 7 times.

Group of Vincristine plus the ethanol extract of *Fructus schisandrae*: mice were dosed intragastrically with 400 mg/kg of the ethanol extract of *Fructus schisandrae*, followed by injection into their abdominal cavities with 0.3 mg/kg of Vincristine within 2 hours, once every two days and consecutively for 7 times.

2. Results 2.1 Effect of *Fructus schisandrae* Together with Doxorubicin on Various Organs of Mice (See Tablet 1)

Mice were put to death and their heart, liver, spleen, kidney and thymus were weighed. It was discovered that the immune organs of antineoplastic agent groups were obviously lighter than those of control group, indicating that antineoplastic agents produce obvious toxicity and side effects on each organ. The immune organs of the groups using the ethanol extract of *Fructus schisandrae* together were heavier to a certain extent than those of control group, indicating that the ethanol extract of *Fructus schisandrae* has potential in reducing toxicity and side effects of antineoplastic agent and in improving immune function.

TABLE 1

Inhibition of the weight decrease of each organ of mice induced by antineoplastic agent by the ethanol extract of *Fructus schisandrae*

|  | Liver(g) | Heart(mg) | Kidney(mg) | Thymus(mg) | Spleen(mg) |
|---|---|---|---|---|---|
| Control group(n = 6) | 1.93 ± 0.365 | 162.2 ± 27.2 | 389.3 ± 58.9 | 98.2 ± 19.1 | 158.7 ± 44.2 |
| Methotrexate group(n = 6) | 1.57 ± 0.192 | 161.8 ± 19.5 | 365.6 ± 27.5 | 53.9 ± 16.2 | 101.6 ± 36.7 |
| Group of Methotrexate plus the ethanol extract of *Fructus schisandrae*(400 mg/kg; n = 6) | 1.96 ± 0.49 | 161.7 ± 22.3 | 375.8 ± 41.6 | 96.1 ± 15.4* | 147.1 ± 22.8* |
| Cisplatin group(n = 6) | 1.78 ± 0.270 | 157.4 ± 24.9 | 313.5 ± 74.88 | 56.3 ± 12.6 | 98.4 ± 22.8 |
| Group of Cisplatin plus the ethanol extract of *Fructus schisandrae*(400 mg/kg; n = 6) | 1.87 ± 0.19 | 168.3 ± 25.6 | 386.3 ± 58.9 | 89.9 ± 11.7* | 151.2 ± 33.5* |
| 5-fluorouracil group | 1.88 ± 0.28 | 159.6 ± 22.6 | 378.6 ± 59.3 | 61.9 ± 10.4 | 102.4 ± 22.8 |
| Group of 5-fluorouracil plus the ethanol extract of *Fructus schisandrae*(400 mg/kg; n = 6) | 1.88 ± 0.34 | 162.5 ± 31.7 | 371.4 ± 35.7 | 97.3 ± 15.2* | 157.1 ± 25.7* |
| Cytoxan group(n = 6) | 1.88 ± 0.36 | 162.6 ± 31.4 | 396.3 ± 54.7 | 49.8 ± 12.4 | 113.5 ± 24.7 |
| Group of Cytoxan plus the ethanol extract of *Fructus schisandrae*(400 mg/kg; n = 6) | 1.82 ± 0.35 | 157.2 ± 34.5 | 381.4 ± 32.5 | 89.7 ± 20.3* | 149.6 ± 31.7* |
| Vincristine group(n = 6) | 1.87 ± 0.33 | 159.5 ± 21.7 | 385.3 ± 85.7 | 58.9 ± 13.3 | 109.5 ± 18.9 |
| Group of Vincristine plus the ethanol extract of *Fructus schisandrae*(400 mg/kg; n = 6) | 1.83 ± 0.46 | 161.6 ± 33.7 | 381.2 ± 62.4 | 89.3 ± 21.1* | 152.5 ± 18.9* |
| Doxorubicin group(n = 10) | 1.51 ± 0.215 | 134.8 ± 19.5 | 335.6 ± 27.5 | 55.8 ± 14.2 | 91.6 ± 35.9 |
| Group of Doxorubicin plus the ethanol extract of *Fructus schisandrae*(400 mg/kg; n = 6) | 1.89 ± 0.26* | 156.4 ± 22.1 | 398.3 ± 66.9* | 89.1 ± 19.6* | 158.7 ± 23.8* |

*indicating that using in combination with ethanol extract of *Fructus schisandrae* had notable significance as compared with using antineoplastic agent alone Doxorubicin group: mice were injected into their abdominal cavities with 4 mg/kg once every two days and consecutively for 7 times.

Group of Doxorubicin plus the ethanol extract of *Fructus schisandrae*: mice were dosed intragastrically with 400 mg/kg of the ethanol extract of *Fructus schisandrae*, followed by injection into their abdominal cavities with 0.3 mg/kg of Vincristine within 2 hours, once every two days and consecutively for 7 times.

2.2 Effects of the Ethanol Extract of *Fructus schisandrae* and Antineoplastic Agent on Apparent Condition of Mice Mice in the group using antineoplastic agent alone were in bad conditions after 7-8 days, manifested as asthenia, listlessness and hypotrichosis. However, mice in the group administering in combination with the extract of *Fructus schisandrae* were relatively active and eutrichosis. These indicated that toxicity and side effects induced by antineoplastic agent could be reduced by the ethanol extract of *Fructus schisandrae*.

Examples 2-5 indicated that the ethanol extract of *Fructus schisandrae* can reduce and prevent the toxicity produced by antibiotics anti-tumor agents. Example 6 indicated that the ethanol extract of *Fructus schisandrae* can reduce and prevent the toxicities of anti-tumor drugs originated from plant, anti-metabolism agents, alkylating agents and platinum drugs.

Example 7

Study on Prevention of Cardio Toxicity of Doxorubicin by Schisandrin B (SchB)

1. Materials and Methods
1.1 Drugs and Agents
Doxorubicin Hydrochloride Injection was obtained from Italy pharmacia Co. (Product No.: 5E2002-D). SchB was obtained from National Institute for the Verification of Pharmaceutical and Biological Products (Product No.: 110765-200407), which was dissolved in 0.5% Poloxamer. CK, CK-MB, LDH and GOT were determined by automatic biochemistry analyzer. Tissue Protein extraction solution was obtained from American Pierce Co. Male ICR mice with a body weight of 25-30 g were obtained from Shanghai Experimental Animal Center.

1.2 Grouping and Administration
162 animals were grouped randomly into 6 groups.
Control group: 24 mice were dosed intragastrically with normal saline at the $1^{st}$-$3^{rd}$ day of the experiment, once a day and each time with 20 ml/kg. At the $3^{rd}$ day, the mice were injected into their abdominal cavities with normal saline within 2 hours after drench.

Group of Schisandrin B (SchB group): 24 mice were dosed intragastrically with SchB at the $1^{st}$-$3^{rd}$ day of the experiment, once a day and each time with 100 mg/kg.

Group of Doxorubicin: 42 mice were dosed intragastrically with normal saline at the $1^{st}$-$3^{rd}$ day of the experiment, once a day and each time with 20 ml/kg. At the $3^{rd}$ day, the mice were injected into their abdominal cavities with Doxorubicin of 25 mg/kg.

Group 1 of Doxorubicin plus Schisandrin B (group 1 of Dox +SchB): 24 mice were dosed intragastrically with SchB at the $1^{st}$-$3^{rd}$ day of the experiment, once a day and each time with 100 mg/kg. At the $3^{rd}$ day, the mice were injected into their abdominal cavities with 25 mg/kg of Doxorubicin 0.5 hours after drench.

Group 2 of Doxorubicin plus Schisandrin B (group 2 of Dox +SchB): 24 mice were dosed intragastrically with SchB at the $1^{st}$-$3^{rd}$ day of the experiment, once a day and each time with 50 mg/kg. At the $3^{rd}$ day, the mice were injected into their abdominal cavities with 25 mg/kg of Doxorubicin 0.5 hours after drench.

Group 3 of Doxorubicin plus Schisandrin B (group 3 of Dox +SchB): 24 mice were dosed intragastrically with SchB at the $1^{st}$-$3^{rd}$ day of the experiment, once a day and each time with 25 mg/kg. At the $3^{rd}$ day, the mice were injected into their abdominal cavities with 25 mg/kg of Doxorubicin 0.5 hours after drench.

1.3 Detection of Serum Myocardium Enzymes
At the $5^{th}$ day (48 hours after injection of Doxorubicin into abdominal cavity), blood were taken from 6 mice of each group. The serum was separated by regular separation. CK, CK-MB, LDH and GOT were determined by automatic biochemistry analyzer.

1.4 Detection of Myocardium MMP
The experimental method was carried out as those described in Example 2 (1.4).

1.5 Survival Rate Observation
The remainder mice were observed for 7 days from the day of Doxorubicin administration and the change of survival rate was recorded.

2. Results
2.1 Effect of Schisandrin B on Serum Myocardium Enzyme Spectrum of Mice with Myocardial Damage Induced by Doxorubicin There were no significant differences between the serum myocardium enzyme spectrum indexes, such as CK, CK-MB, LDH, GOT, etc., of control group and those of SchB group (P>0.05). The 4 serum enzyme indexes of Doxorubicin group were significantly higher than those of control group and Sch B group (P<0.05). The serum enzyme indexes of the three dosage groups using in combination with Sch B were decreased to a certain extent as compared with those of the group using Doxorubicin alone. In particular, the 4 serum enzyme indexes of the group using 100 mg/kg of Sch B for 3 times in combination with Doxorubicin had no significant difference as compared with those of control group (P>0.05). The 4 serum enzyme indexes of the group using 100 mg/kg of Sch B for 3 times in combination with Doxorubicin, however, had significant difference as compared with the significantly increased serum enzymes produced by the group using Doxorubicin alone (P<0.05). The CK and CK-MB indexes of the group using 50 mg/kg of Sch B for 3 times in combination with Doxorubicin and those of the group using 25 mg/kg of Sch B for 3 times in combination with Doxorubicin had significant difference as compared with the group using Doxorubicin alone (P<0.05). See FIG. 10-13. These indicated that the cardio toxicity induced by Doxorubicin could be prevented by Sch B.

Figure 14:
FIG. 14 shows that schisandrin B can inhibit the increase of mouse left ventricular myocardium matrix metalloproteinase MMP-2 activity induced by Doxorubicin.

2.2 Detection Results of the Activity of Left Ventricular Myocardium Metalloproteinase No left ventricular myocardium matrix metalloproteinase (MMP-2) activity were detected both in the normal control group and in Sch B group. The MMP-2 activity of the Doxorubicin group was increased obviously. The MMP-2 activity in the three dosage groups using Sch B in combination with Doxorubicin were inhibited significantly, wherein the inhibition effect of the group using 100 mg/kg of Sch B together with Doxorubicin was the best. See FIG. 14. These results indicated that the cardio toxicity induced by Doxorubicin could be prevented by Sch B.

Figure 15:
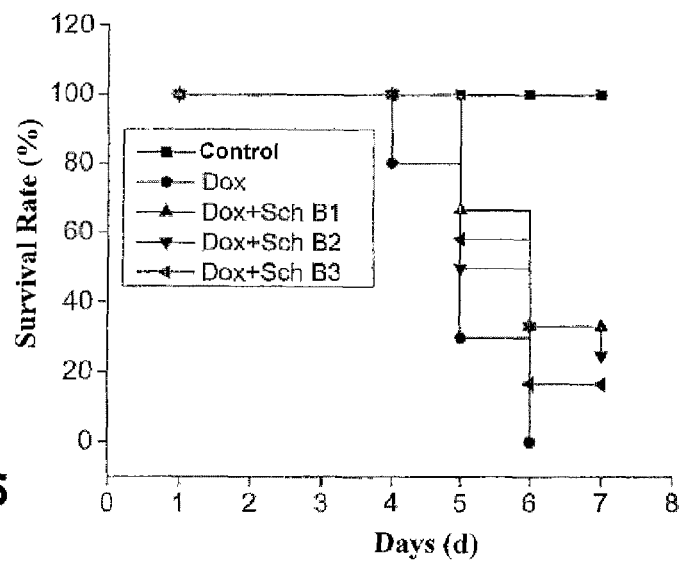
FIG. 15 shows that schisandrin B can inhibit the death of mouse induced by Doxorubicin.

2.3 Effect of Sch B on Survival Rate of Mice with Acute Toxicity Induced by Doxorubicin The death of mice in the Doxorubicin group occurred on the $4^{th}$ day, and the death of mice in the three groups using Sch B together with Doxorubicin occurred on the $5^{th}$ day. On the $7^{th}$ day, the survival rate of the Doxorubicin group was 0, the survival rate of the group using 100 mg/kg of Sch B for 3 times together with Doxorubicin was 33.3% (P<0.01), the survival rate of the group using 50 mg/kg of Sch B for 3 times together with Doxorubicin was 25% (P<0.01), and the survival rate of the group using 25 mg/kg of Sch B for 3 times together with Doxorubicin was 16.67% (P<0.05). See FIG. 15. These results indicated that toxicity and side effects induced by Doxorubicin could be obviously reduced by Sch B.

Example 8

Five Dibenzocyclooctadiene Lignans can Prevent Other Toxicity and Side Effects of Doxorubicin 1. Materials and Methods
1.1 Experimental Materials
Doxorubicin Hydrochloride Injection was obtained from Italy pharmacia Co. Six Dibenzocyclooctadiene lignans were obtained from National Institute for the Verification of Pharmaceutical and Biological Products (Product No.: 110765-200407), which were dissolved in 0.5% Poloxamer. Female ICR mice with a body weight of 25-30 g were obtained from Shanghai Experimental Animal Center, which were grouped randomly into 4 groups, 10 mice per group.

1.2 Animal Grouping and the Ways and Routines of Administration

Control group: 10 mice were injected into their abdominal cavities with normal saline once every two days and consecutively for 7 times.

Group of Doxorubicin (Dox group): 10 mice were injected into their abdominal cavities with 2 mg/kg of Doxorubicin once every two days, consecutively for 7 times. Group 1 of Doxorubicin plus Schisandrin B (group 1 of Dox +SchB): 10 mice were dosed intragastrically with 50 mg/kg of Sch B, followed by injection into their abdominal cavities with 2 mg/kg of Doxorubicin within two hours, once every two days and consecutively for 7 times.

Group 2 of Doxorubicin plus Schisandrin B (group 2 of Dox +SchB): 10 mice were dosed intragastrically with 100 mg/kg of Sch B, followed by injection into their abdominal cavities with 2 mg/kg of Doxorubicin within two hours, once every two days and consecutively for 7 times.

Group of Doxorubicin plus Schisandrin A: 10 mice were dosed intragastrically with 100 mg/kg of Schisandrin A, followed by injection into their abdominal cavities with 2 mg/kg of Doxorubicin within two hours, once every two days and consecutively for 7 times.

Group of Doxorubicin plus Schisandrin C: 10 mice were dosed intragastrically with 100 mg/kg of Schisandrin C, followed by injection into their abdominal cavities with 2 mg/kg of Doxorubicin within two hours, once every two days and consecutively for 7 times.

Group of Doxorubicin plus Schizandrol A: 10 mice were dosed intragastrically with 100 mg/kg of Schizandrol A, followed by injection into their abdominal cavities with 2 mg/kg of Doxorubicin within two hours, once every two days and consecutively for 7 times.

Group of Doxorubicin plus Schizandrol B: 10 mice were dosed intragastrically with 100 mg/kg of Schizandrol B, followed by injection into their abdominal cavities with 2 mg/kg of Doxorubicin within two hours, once every two days and consecutively for 7 times.

2. Results 2.1 Effect of 5 Dibenzocyclooctadiene Lignans in Combination with Doxorubicin on Various Organs of Mice (See Tablet 2)

Mice were put to death and their heart, liver, spleen, kidney and thymus were weighed. It was discovered that each organ of the Dox group were obviously lighter than those of the other groups, indicating that Doxorubicin produced obvious toxicity and side effects on each organ. The organs of groups using dibenzocyclooctadiene lignan together with Doxorubicin were heavier to a certain extent than those of the Dox group, indicating that dibenzocyclooctadiene lignans had the potential in reducing toxicity and side effects of Doxorubicin and in improving immune function.

TABLE 2

Inhibition of the weight decrease of each organ of mice induced by Doxorubicin by 5 dibenzocyclooctadiene lignans

|  | Liver(g) | Heart(mg) | Kidney(mg) | Thymus(mg) | Spleen(mg) |
|---|---|---|---|---|---|
| Control group(n = 10) | 1.89 ± 0.436 | 160.2 ± 29.5 | 394.8 ± 60.99 | 95.1 ± 17.3 | 154.7 ± 51.0 |
| Group of Doxorubicin(n = 10) | 1.51 ± 0.215 | 134.8 ± 19.5 | 335.6 ± 27.5 | 55.8 ± 14.2 | 91.6 ± 35.9 |
| Group 1 of Doxorubicin plus Schisandrin B (50 mg/kg; n = 10) | 1.66 ± 0.249 | 130.7 ± 20.4 | 384.8 ± 40.4* | 57.1 ± 10.7 | 108.1 ± 33.7 |
| Group 2 of Doxorubicin plus Schisandrin B (100 mg/kg; n = 10) | 1.78 ± 0.270* | 147.4 ± 24.9 | 393.5 ± 74.88* | 73.8 ± 20.5* | 130.4 ± 42.8* |
| Group of Doxorubicin plus Schisandrin A (100 mg/kg; n = 10) | 1.71 ± 0.16* | 151.4 ± 21.6 | 389.2 ± 69.8* | 69.6 ± 21.7* | 144.6 ± 43.5* |
| Group of Doxorubicin plus Schisandrin C (100 mg/kg; n = 10) | 1.82 ± 0.21* | 158.4 ± 25.5 | 373.5 ± 68.2* | 76.9 ± 19.5* | 129.4 ± 32.8* |
| Group of Doxorubicin plus Schizandrol A (100 mg/kg; n = 10) | 1.83 ± 0.310* | 164.4 ± 34.9 | 401.3 ± 84.9 | 83.9 ± 25.3* | 137.4 ± 42.6* |
| Group of Doxorubicin plus Schizandrol B (100 mg/kg; n = 10) | 1.85 ± 0.38* | 161.5 ± 31.6 | 395.2 ± 84.66* | 85.8 ± 22.3* | 133.5 ± 38.68* |

*indicating that as compared with the group of Doxorubicin, the difference was significant($P < 0.05$)

2.2 Effects of Dibenzocyclooctadiene Lignans and Doxorubicin on Apparent Conditions of Mice Mice in the group using Doxorubicin alone were in bad conditions after 7-8 days, manifested as asthenia, listlessness and hypotrichosis. However, mice in the group administered with Doxorubicin in combination with dibenzocyclooctadiene lignans were relatively active and eutrichosis. These indicated that toxicity and side effects induced by antineoplastic agent could be reduced by dibenzocyclooctadiene lignans.

The antineioplastic used in the Example was Doxorubicin. Doxorubicin has not only the common toxicity and side effects of antineioplastics, e.g. immune inhibition, marrow inhibition, etc., but also cardiovascular toxicity of the medicine with an anthracycline core structure. As a result, Doxorubicin can well reflect the toxicity and side effects of antineoplastic agent.

Example 9

Six Dibenzocyclooctane Lignans can Reduce Cardio Toxicity of Induced by Daunorubicin Experimental method: ICR mice were purchased from Shanghai Experimental Animal Center. Schisandrin A, Schisandrin B, Schisandrin C, Schisantherin A, Schizandrol A, and Schizandrol B were prepared with 0.5% poloxamer as 1 g/ml mutterlauge respectively. The animals were grouped into 7 groups, 15 mice each group. Each mouse in group 1 was dosed intragastrically with 100 µl solvent (0.5% poloxamer), each mouse in group 2 was dosed intragastrically with 100 µl Schisandrin A, each mouse in group 3 was dosed intragastrically with 100 µl Schisandrin B, each mouse in group 4 was dosed intragastrically with 100 µl Schisandrin C, each mouse in group 5 was dosed intragastrically with 100 µl Schisantherin A, each mouse in group 6 was dosed intragastrically with 100 µl Schizandrol A, and each mouse in group 7 was dosed intragastrically with 100 µl Schizandrol B, and 3 hours after administration of solvent or the above dibenzocyclooctane lignans, mice in each group were injected with 4 mg/kg Daunorubicin through tail vein. The above administrations were carried out once every 7 days for 10 times totally. The mice were put to death one week after the last time of injection and their hearts were taken out. The heart was fixed with 4% paraform. The operation steps were the same as those in Example 3.

Figure 16:
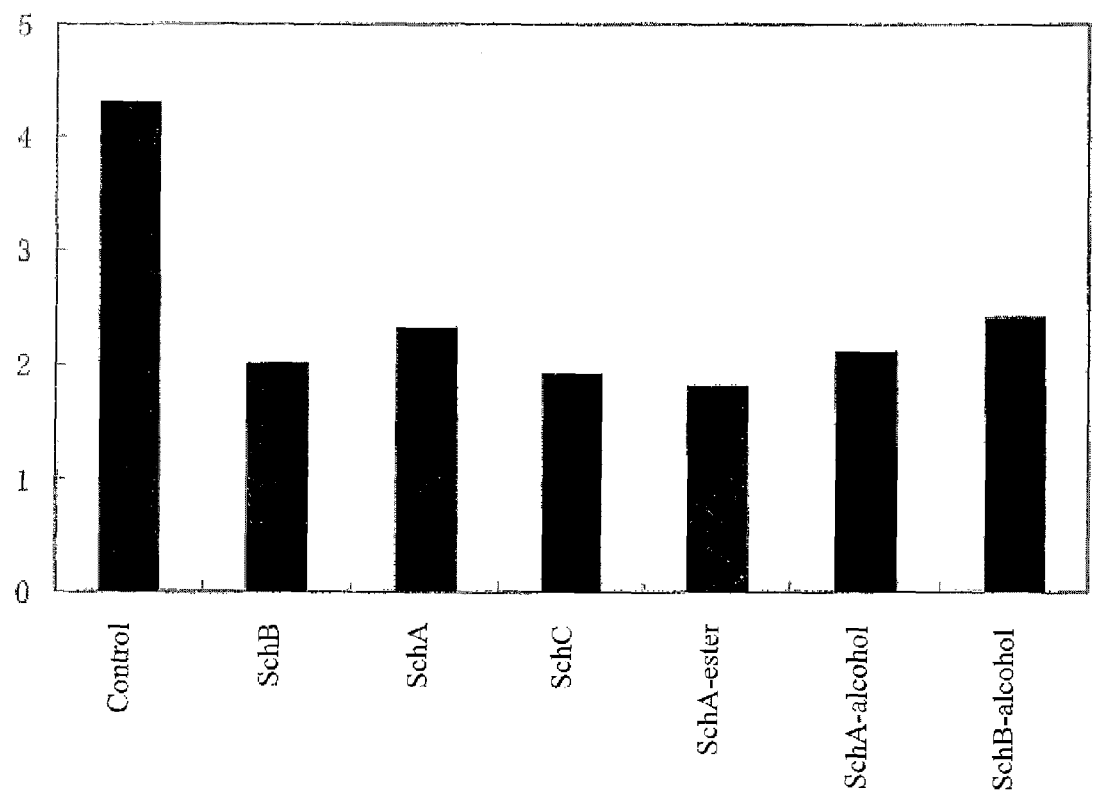
FIG. 16 shows that the prevention of cardio toxicity of mice induced by Daunorubicin by six dibenzocyclooctane lignans.

Results: As indicated in FIG. 16, the cardio toxicity induced by Daunorubicin could be significantly reduced by the 6 dibenzocyclooctane lignans, indicating that the 6 dibenzocyclooctane lignans had significant prevention effects on cardio toxicity induced by Daunorubicin.

Example 10

Dibenzocyclooctane Lignans can Prevent and Reduce Other Toxicity and Side Effects of Antineoplastic Agent The above Examples indicated that dibenzocyclooctane lignans can reduce and prevent the toxicity of antibiotics anti-tumor agents. This Example indicateds that dibenzocyclooctane lignans can also reduce and prevent the toxicities of anti-tumor drugs originated from plant, antimetabolism agents, alkylating agents and platinum drugs.

1. Materials and Methods 1.1 Experimental Materials

Vincristine, Methotrexate, Cisplatin, Cytoxan, and 5-fluorouracil were from Shanghai Pharmacy Co. 6 dibenzocyclooctadiene lignans were bought from National Institute for the Verification of Pharmaceutical and Biological Products, which were dissolved in 0.5% Poloxamer. ICR mice, body weight 20-25 g, were obtained from Shanghai Experimental Animal Center. The mice were divided randomly as following, 6 mice per group.

1.2 Animal Grouping and the Way and Routine of Administration

Control group: mice were injected into their abdominal cavities with normal saline once every two days, consecutively for 7 times.

Methotrexate group: mice were injected into their abdominal cavities with 2 mg/kg once every two days, consecutively for 7 times.

Group of Methotrexate plus Schisandrin B: mice were dosed intragastrically with 100 mg/kg of Schisandrin B, followed by injection into their abdominal cavities with 2 mg/kg of Methotrexate within two hours, once every two days and consecutively for 7 times.

Cisplatin group: mice were injected into their abdominal cavities with 2 mg/kg once every two days, consecutively for 7 times.

Group of Cisplatin plus Schisandrin A: mice were dosed intragastrically with 100 mg/kg of Schisandrin A, followed by injection into their abdominal cavities with 2 mg/kg of Cisplatin within two hours, once every two days, consecutively for 7 times.

5-fluorouracil group: mice were injected into their abdominal cavities with 30 mg/kg once every two days, consecutively for 7 times.

Group of 5-fluorouracil plus Schisandrin C: mice were dosed intragastrically with 100 mg/kg of Schisandrin C, followed by injection into their abdominal cavities with 30 mg/kg of 5-fluorouracil within two hours, once every two days, consecutively for 7 times.

Cytoxan group: mice were injected into their abdominal cavities with 30 mg/kg once every two days, consecutively for 7 times.

Group of Cytoxan plus Schisantherin A: mice were dosed intragastrically with 100 mg/kg of Schisantherin A, followed by injection into their abdominal cavities with 30 mg/kg of Cytoxan within two hours, once every two days and consecutively for 7 times.

Vincristine group: mice were injected into their abdominal cavities with 0.3 mg/kg once every two days, consecutively for 7 times.

Group of Vincristine plus Schizandrol A: mice were dosed intragastrically with 100 mg/kg of Schizandrol A, followed by injection into their abdominal cavities with 0.3 mg/kg of Vincristine within two hours, once every two days, and consecutively for 7 times.

2. Results 2.1 Effect of 6 Dibenzocyclooctadiene Lignans in Combination with Doxorubicin on Various Organs of Mice (See Tablet 3)

Mice were put to death and their heart, liver, spleen, kidney and thymus were weighed. It was discovered that the immune organs of antineoplastic agent groups were obviously lighter than those of control group, indicating that antineoplastic agents produce obvious toxicity and side effects on each organ. The immune organs of the groups using dibenzocyclooctadiene lignans together were heavier to a certain extent than those of control group, indicating that dibenzocyclooctadiene lignans have potential in reducing toxicity and side effects of antineoplastic agents and in improving immune function.

TABLET 3

Inhibition of weight decrease of each organ of mice induced by antineoplastic agents by 6 dibenzocyclooctadiene lignans

|  | Liver(g) | Heart(mg) | Kidney(mg) | Thymus(mg) | Spleen(mg) |
|---|---|---|---|---|---|
| Control group(n = 6) | 1.93 ± 0.365 | 162.2 ± 27.2 | 389.3 ± 58.9 | 98.2 ± 19.1 | 158.7 ± 44.2 |
| Methotrexate group (n = 6) | 1.57 ± 0.192 | 161.8 ± 19.5 | 365.6 ± 27.5 | 53.9 ± 16.2 | 101.6 ± 36.7 |

TABLET 3-continued

Inhibition of weight decrease of each organ of mice induced by antineoplastic agents by 6 dibenzocyclooctadiene lignans

| | Liver(g) | Heart(mg) | Kidney(mg) | Thymus(mg) | Spleen(mg) |
|---|---|---|---|---|---|
| Group of Methotrexate plus Schisandrin B (100 mg/kg; n = 6) | 1.86 ± 0.249 | 159.7 ± 21.4 | 384.4 ± 40.4 | 86.1 ± 12.6* | 138.1 ± 31.7* |
| Cisplatin group(n = 6) | 1.78 ± 0.270 | 157.4 ± 24.9 | 313.5 ± 74.88 | 56.3 ± 12.6 | 98.4 ± 22.8 |
| Group of Cisplatin plus Schisandrin A (100 mg/kg; n = 6) | 1.89 ± 0.18 | 158.9 ± 23.4 | 383.2 ± 67.6 | 89.7 ± 13.8* | 156.6 ± 42.6* |
| 5-fluorouracil group | 1.88 ± 0.28 | 159.6 ± 22.6 | 378.6 ± 59.3 | 61.9 ± 10.4 | 102.4 ± 22.8 |
| Group of 5-fluorouracil plus Schisandrin C (100 mg/kg; n = 6) | 1.89 ± 0.32 | 162.1 ± 33.8 | 391.4 ± 45.8 | 89.8 ± 14.2* | 147.4 ± 22.6* |
| Cytoxan group(n = 6) | 1.88 ± 0.36 | 162.6 ± 31.4 | 396.3 ± 54.7 | 49.8 ± 12.4 | 113.5 ± 24.7 |
| Group of Cytoxan plus Schisantherin A (100 mg/kg; n = 6) | 1.89 ± 0.39 | 169.2 ± 32.8 | 391.2 ± 35.6 | 84.7 ± 21.4* | 143.5 ± 35.8* |
| Vincristine group(n = 6) | 1.87 ± 0.33 | 159.5 ± 21.7 | 385.3 ± 85.7 | 58.9 ± 13.3 | 109.5 ± 18.9 |
| Group of Vincristine plus Schizandrol A (100 mg/kg; n = 6) | 1.79 ± 0.36 | 162.3 ± 42.6 | 386.2 ± 64.9 | 81.9 ± 12.1* | 143.5 ± 19.8* |

*indicating that as compared with using antineoplastic agent alone, using together with dibenzocyclooctane lignan had notable significance 2.2 Effects of 5 Dibenzocyclooctadiene Lignans and Antineoplastic Agents on Apparent Conditions of Mice Mice in the group using antineoplastic agent alone were in bad conditions after 7-8 days, manifested as asthenia, listlessness and hypotrichosis. However, mice in the group administered in combination with dibenzocyclooctadiene lignans were relatively active and eutrichosis. These indicated that toxicity and side effects induced by antineoplastic agent could be reduced by dibenzocyclooctane lignans.

I claim:

1. A method of reducing cardiovascular toxicity of an anthracycline antibiotic in a patient in need thereof comprising administering a therapeutically effective amount of Schisandrin B to said patient 6-72 hours prior to administering an anthracycline antibiotic to the patient.

2. The method of claim 1 wherein the anthracycline antibiotic is selected from the group consisting of aclarubicin, amrubicin, carubicin, daunorubicin, detorubicin, doxorubicin, epirubicin, esorubicin, galarubicin, idarubicin, ladirubicin, leurubicin, medorubicin, nemorubicin, pirarubicin, rodorubicin, sabarubicin, valrubicin and zorubicin.

* * * * *